(12) United States Patent
Osypka et al.

(10) Patent No.: US 7,398,125 B2
(45) Date of Patent: Jul. 8, 2008

(54) SUTURE COLLAR WITH A FLEXIBLE CONSTRAINING MEANS

(75) Inventors: Peter Osypka, Earl-H.-Wood-Strasse 1, Rheinfelden-Herten (DE) 79618; Hans Gerstmann, Lörrach (DE)

(73) Assignee: Peter Osypka, Rheinfelden-Herten (DE)

( * ) Notice: Subject to any disclaimer, the term of this patent is extended or adjusted under 35 U.S.C. 154(b) by 218 days.

(21) Appl. No.: 11/398,251

(22) Filed: Apr. 5, 2006

(65) Prior Publication Data

US 2008/0009928 A1    Jan. 10, 2008

(30) Foreign Application Priority Data

Apr. 9, 2005    (DE) .................. 10 2005 016 364

(51) Int. Cl.
*A61N 1/00* (2006.01)

(52) U.S. Cl. .................. 607/119; 607/116; 604/174

(58) Field of Classification Search ............... 24/115 R, 24/122.3, 715.3; 607/116, 119; 285/21.1, 285/24, 39, 124.4, 140.1, 154.2, 242, 307; 174/15.7, 151, 669; 600/585; 606/1, 46; 405/184; 137/355.16
See application file for complete search history.

(56) References Cited

U.S. PATENT DOCUMENTS 2,127,903 A * 8/1938 Bowen ..................... 606/154

| 4,287,891 | A | * | 9/1981 | Peters | 604/174 |
| 4,516,584 | A | * | 5/1985 | Garcia | 607/119 |
| 4,553,961 | A | * | 11/1985 | Pohndorf et al. | 604/175 |
| 4,672,979 | A | * | 6/1987 | Pohndorf | 607/126 |
| 5,152,298 | A | * | 10/1992 | Kreyenhagen et al. | 607/116 |
| 5,476,493 | A | | 12/1995 | Muff | |
| 5,897,585 | A | * | 4/1999 | Williams | 607/122 |
| 2006/0173520 | A1 | * | 8/2006 | Olson | 607/115 |

* cited by examiner

*Primary Examiner*—Terrell McKinnon
*Assistant Examiner*—Luther G Behringer
(74) *Attorney, Agent, or Firm*—Volpe and Koenig, P.C.

(57) ABSTRACT

A device for fastening an electrode in the pacemaker bed before the entry of the electrode into a vein is provided, and includes a sheath having two parts and, with a hose extending through their interior. The two parts and of the sheath are profiled at the contacting edges of a common separating point so that they are fixed in reference to one another in the rotational direction until a user pulls them apart beyond the axial extension of the profiling. In this pulled-apart position the parts of the sheath can be rotated in reference to one another under torsion of the hose and subsequently, due to the restoring force of the hose, will be again guided together axially, which reduces the interior cross-section of the hose and allows a form-fitting grasping the electrode extending therethrough.

13 Claims, 5 Drawing Sheets

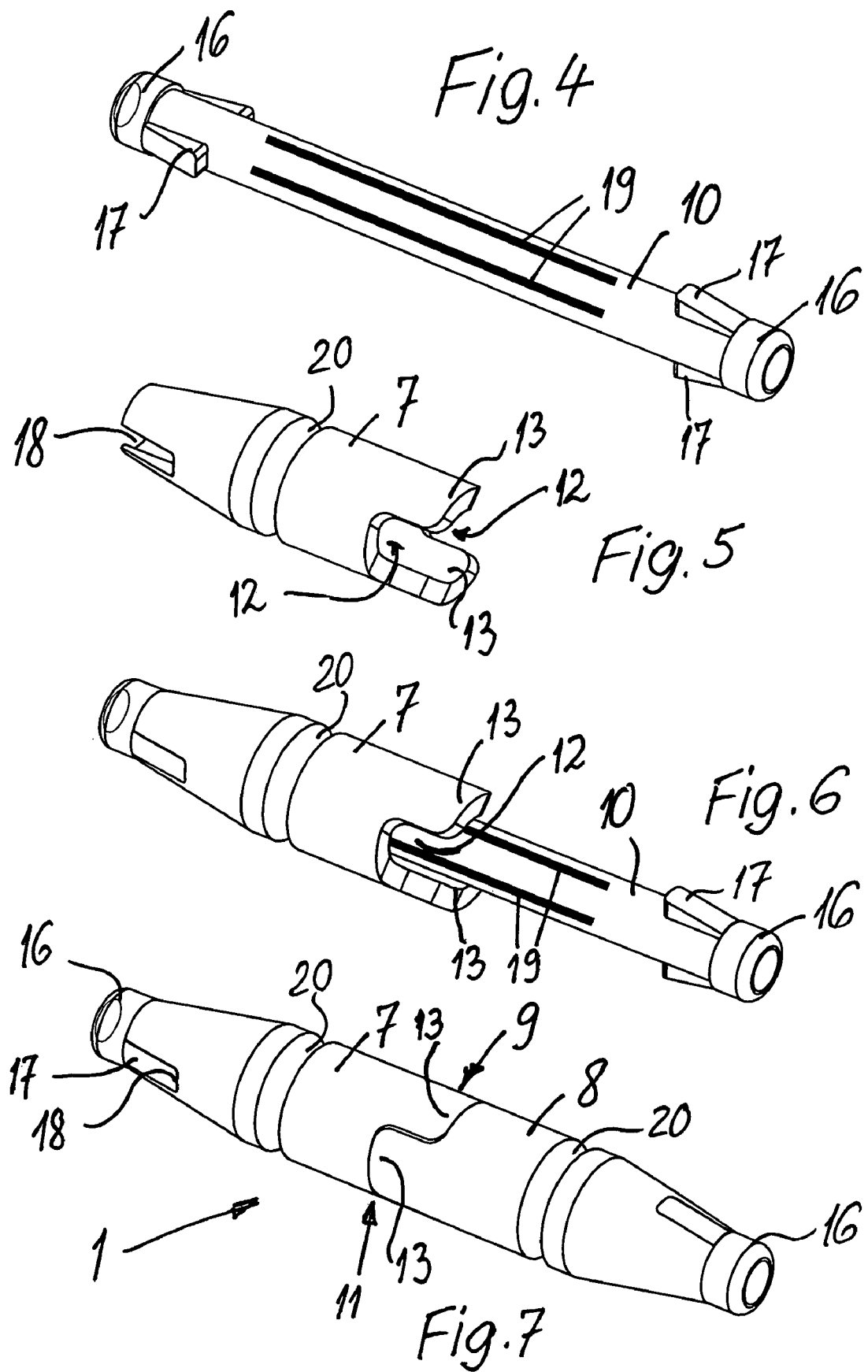

SUTURE COLLAR WITH A FLEXIBLE CONSTRAINING MEANS

BACKGROUND

The invention relates to a device for affixing an electrode, in particular a pacemaker electrode, in the pacemaker bed prior to the entry of the electrode into the vein (ligature protection) having a sheath, which is provided with an interior cavity extending in the axial direction for accepting an electrode, said cavity being reducible in its cross-section in order to fasten the electrode in the operational position, with the sheath containing an elastic hose, stretchable in an axial direction against a restoring force, which simultaneously forms the interior longitudinal cavity for accepting the electrode and, along a separating point extending at its circumference, the sheath being divided in the longitudinal direction into at least two parts that can be moved in reference to one another in the axial direction.

A device of this type is known from the U.S. Pat. No. 5,476,493. Here, the two parts of the sheath are inserted into one another in a telescoping manner and can be displaced, and a pressure spring is inserted between the face of the interior part and a stop of the other part, its force moving the two components apart in the axial direction, stretching the hose, with the hose simultaneously being contracted in its middle area due to its stretching and thus grasping the electrode in a clamping fashion. This represents an expensive and easily malfunctioning construction, which depends on the good gliding ability of the two parts in reference to one another and primarily from the additionally integrated spring, with its assembly being difficult.

From the U.S. Pat. No. 5,152,298 a device of a similar type for fastening an electrode is known, in which a sheath-shaped part with a continuous interior cavity for accepting the electrode is provided in three sections. In the first section, a widening of the interior cavity is provided. An axially subsequent section, reduced in its exterior circumference, is provided with an exterior thread, and an axially continuing section comprises an elastic material and can be pressed against the electrode with the help of a nut, which through rotation and axial displacement, compresses the external thread in the radial direction. This construction is also to be considered relatively expensive and requires a high degree of care during the operation of the nut.

SUMMARY

Therefore, the objective is to provide a device of the type mentioned at the outset in which a pressure spring for the telescope-like displacement of the two parts of the sheath is avoided, and a good clamping between the hose and the electrode is still enabled.

This objective is attained in a device of the type defined at the outset in that the separation point between two parts of the sheath in reference to a diametral circle plane alternate to opposing sides, so that the face ends of the rims of the parts of the sheath are profiled such that they are connected in a form-fitting manner and that the parts can be pulled apart in the axial direction against the restoring force of the elastic hose holding them together to such an extent that the opposite profiling is separated and the two parts can be rotated by twisting or turning the elastic hose and can be refastened in the rotated position against the rotating motion in contact with each other.

In order to clamp the sheath to the electrode and thus also to axially fastening the electrode in reference to said sheath and thus to the ligature protection, an axial motion of the two parts can be performed, causing them to be separated to such an extent that they can be rotated in reference to one another. This leads to a torsion and thus to a reduction in the cross-section of the hose, which therefore can grasp the electrode in a force-fitting manner with its interior cross-section, when the two parts of the sheath are moved apart from one another after a slight tensile motion and subsequently are rotated in reference to one another to such an extent that after their renewed contact they include the twisted hose in their interior. It is obvious that the opening through the hose is reduced when it is twisted or rotated. This knowledge is used by the invention such that a force-fitting connection of the sheath, which is divided into at least two parts, to an electrode is effected by using the hose located inside the sheath.

This eliminates the necessity for the two parts of the sheath to be inserted into one another telescopically and for a pressure spring to be arranged in their interior. Rather, the parts of the sheath in the area of the separation point can be of with identical cross-sections and thus can directly or indirectly contact one another in the axial direction and/or at their end faces. Due to the elasticity and the preliminary tension of the hose, which is caused or enhanced by the torsion, the two parts are held together sufficiently tight so that the faces contacting one another are also secured against a restoring torsion based on their profiling.

Here, it is beneficial for the profiling at the separation point of the parts of the sheath to comprise recesses or protrusions, tongues, or the like extending in the axial direction, with the tongues of the one part form-fittingly matching the recesses of the other part, in particular, and axially engaging the operational position. Here, said tongues and recesses extending in the axial direction can be formed such that they are complementary, i.e. that the sheath in spite of its division into two parts has a closed and smooth surface even in the area of the separation point.

One embodiment can provide that two tongues are provided protruding in the axial direction on one part and that the other part includes two matching indentations, which themselves are limited by tongues, fitting between the tongues of the first part. Here, the tongues and recesses can are at a regular distance from one another in the circumferential direction and two tongues are arranged off-set in reference to one another by 180°, three tongues by 120°, etc. Appropriately sized rotational movements are possible after the two parts are pulled apart, i.e. only two tongues off-set by 180° at the two parts with the matching recesses allow a rotation of the two parts by 180° or by 360° etc. When more tongues and recesses are provided, smaller rotational steps can be performed, or several of them can be performed in order to cause sufficient twisting of the hose.

A modified embodiment of the invention can comprise the parts of the sheath being provided at their contacting edges with matching gear wheel teeth. On the one hand, only relatively small axial motion is necessary in order to separate the two parts from their mutual torsion lock and, on the other hand, practically arbitrarily small or large relative rotational movements are possible, depending on the number of teeth and the height of the mutual gear teeth.

Here, the teeth of the gear wheel embodied as parts on the sheath and the recesses between the teeth each be provided approximately angular or triangle-shaped, so that the tip of one tooth fits into a correspondingly angular tooth gap, which again results in a closed surface of the two-part sheath in the operational state.

End stops belonging to the sheath can each be mounted at the elastic hose, which serve as counter stops for parts of the sheath arranged on the hose between the end stops, with a torsion lock being provided between the end stops and/or the hose, on the one hand, and the parts of the sheath, on the other hand. Therefore, the end stops hold the parts of the sheath together and the torsion lock provided here allows the transfer of the torsion forces to the parts of the sheath via the end stops to the hose. The necessary transfer of the torsion force onto the hose is also ensured by the mutual fastening between the end stop and the hose itself.

At the end stops, for example, a spring strip can protrude in the axial direction, which form-fittingly matches into an open groove at the face of the matching part of the sheath or the end stop can be provided with a recess, with a protrusion of the part of the sheath engaging in the operational position and/or the contact points of the end stops and the parts of the sheath can be profiled to be form-fitting in reference to one another.

An advantageous embodiment for easing the torsion of the hose can also provide for the elastic hose to have one or more slits extending particularly axially over at least part of its relaxed length, which are deformed during the rotation of the parts of the sheath approximately in one or more helical lines. By such slits in the hose, it is possible that even after its torsion surfaces develop on the inside by the surface-like pressure against the electrode, an even distribution of the clamping power over the circumference of the electrode can be achieved.

It is advantageous for the exterior of the parts of the sheath to be roughened or be provided with grooves or flutes or profiles so that a user can grasp the two parts of the sheath and also can pull them apart axially against a stronger resistance and rotate them in reference to one another without slipping. However, a material may also be selected, which is provided with a respectively high friction coefficient.

It should also be mentioned that at the exterior of at least one part of the sheath, preferably at both parts of the sheath, a circular groove or the like can be provided for mounting suture material for fastening the device in the pacemaker bed.

Here, such circular grooves can also facilitate the grasping and pulling apart against the restoring force of the hose.

Primarily when combining individual or several of the above-described features and measures a device results having a sheath divided into two parts and a hose located therein, which is simple in its construction because no telescopic displacement of the parts of the sheath is necessary and no pressure spring is required on the inside in order to move them apart. Rather, the user can separate the profiling and coupling mutually effective in the torsion direction of the two parts by axially pulling them apart, subsequently rotating them in reference to one another, thus distorting the hose located in the interior, and reduce its cross-section so that the electrode extending therein is grasped and/or fastened in a force-fitting manner.

BRIEF DESCRIPTION OF THE DRAWINGS

In the following, exemplary embodiments of the invention are explained in greater detail using the drawing. In partially schematic representation, they show:

FIG. 4 is a view of an elastic hose with end stops without the two parts of the sheath, FIG. 5 is a view of a part of the sheath independent from the hose and the end stops, FIG. 6 is a view of the arrangement of one part of the sheath on the hose and its relation to the end stop, FIG. 7 is a view of the finished sheath with the two parts of the sheath form-fittingly engaging at the two contact points, which are held at the opposite ends of the end stops of the hose.

DETAILED DESCRIPTION OF THE PREFERRED EMBODIMENTS

Figure 1:
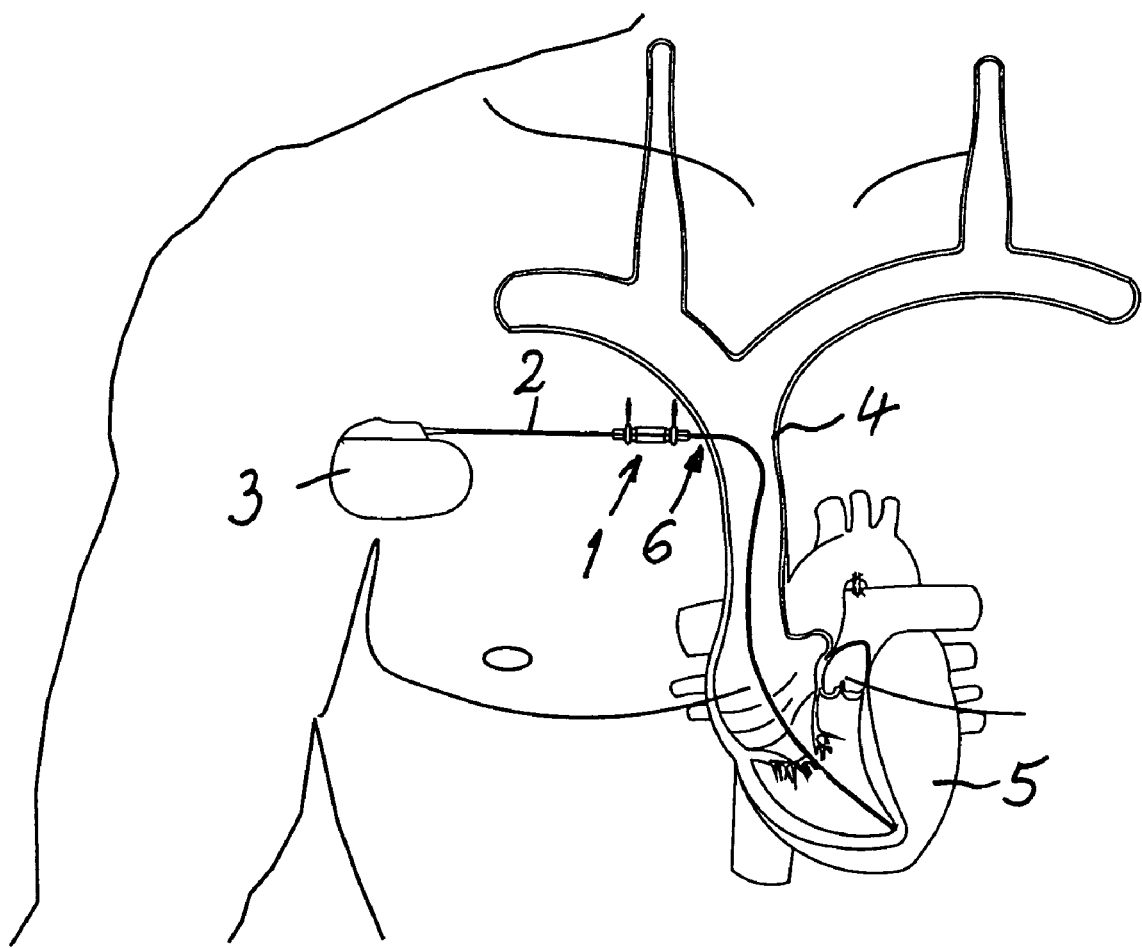
FIG. 1 is a view of a pacemaker and a pacemaker electrode extending therefrom through the pacemaker bed to a vein, and from said vein into the interior of the heart of the patient, which has been fastened shortly prior to the entry into the vein using the device according to the invention.

A device, in its entirety named 1, serves to fasten an electrode 2, in the exemplary embodiment a pacemaker electrode, in the pacemaker bed, with the electrode 2 extending from the pacemaker 3 through the pacemaker bed to a vein 4 and through it into the heart 5. The device 1 is located shortly before the entry 6 of the electrode into the vein 4. Here, the device 1 serving as a ligature protection is provided with a sheath 9 comprising two parts 7 and 8 of the sheath, having an interior cavity extending in the axial direction for accepting the electrode 2, and the interior cavity can be reduced in its cross-section for fastening the electrode 2 in its operational position so that a force-fitting connection develops between the electrode 2 and the interior cavity and/or the parts 7 and 8 of the sheath.

Figure 11:
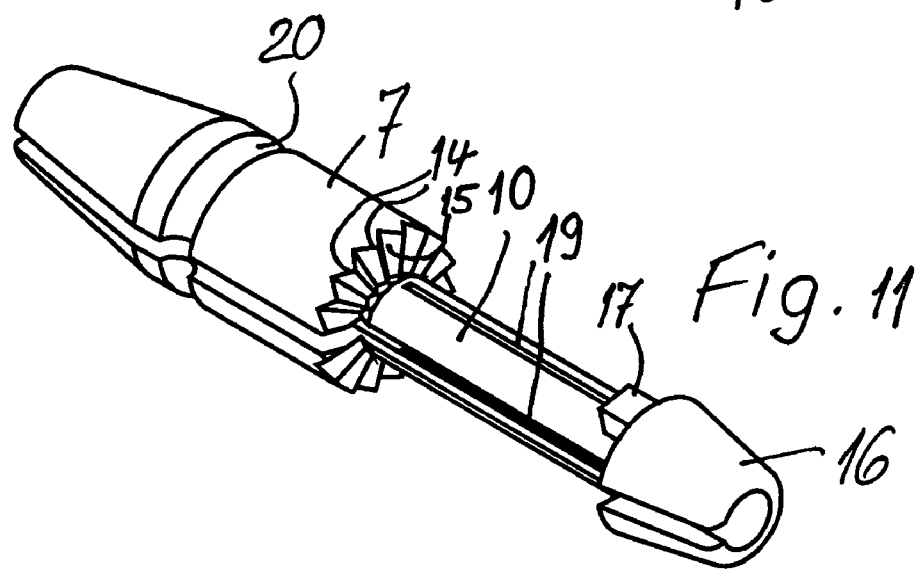
FIG. 11 is a view of the hose located inside the sheath with an end stop and one of the two parts of the sheath, which is already in the operational position.
Figure 12:
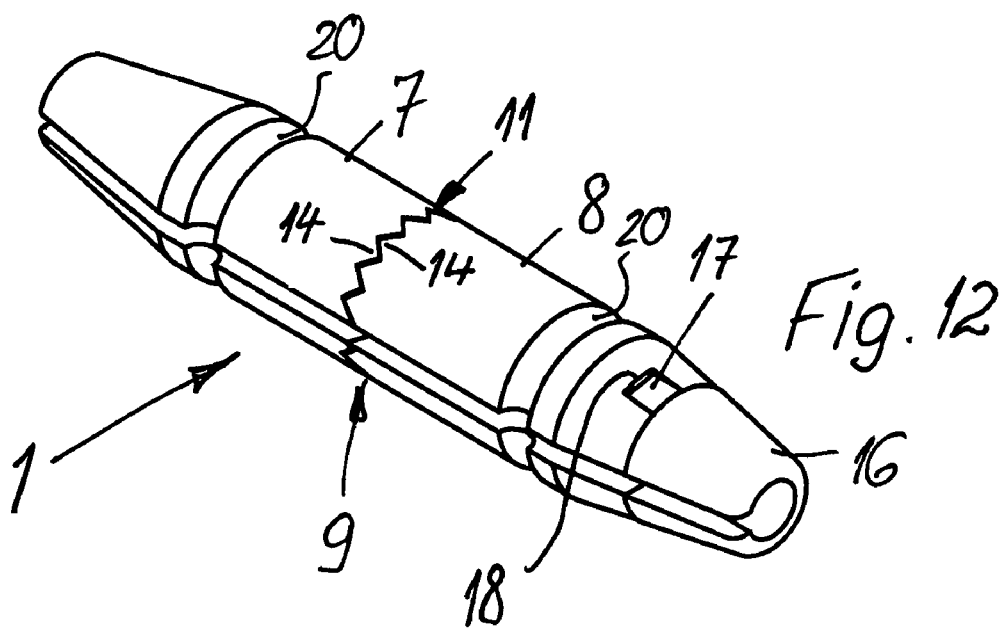
FIG. 12 is a schematic representation of the sheath divided into two parts, with both parts at their contact point being connected to one another in a toothed manner.

Here the sheath named 9 in its entirety, further comprises an elastic hose 10 that can be stretched in the axial direction against the restoring force and/or the elasticity of its material, which is particularly well discernible in the FIGS. 4, 6, and 11 and simultaneously forms the interior longitudinal cavity for accepting the electrode 2.

Figure 3:
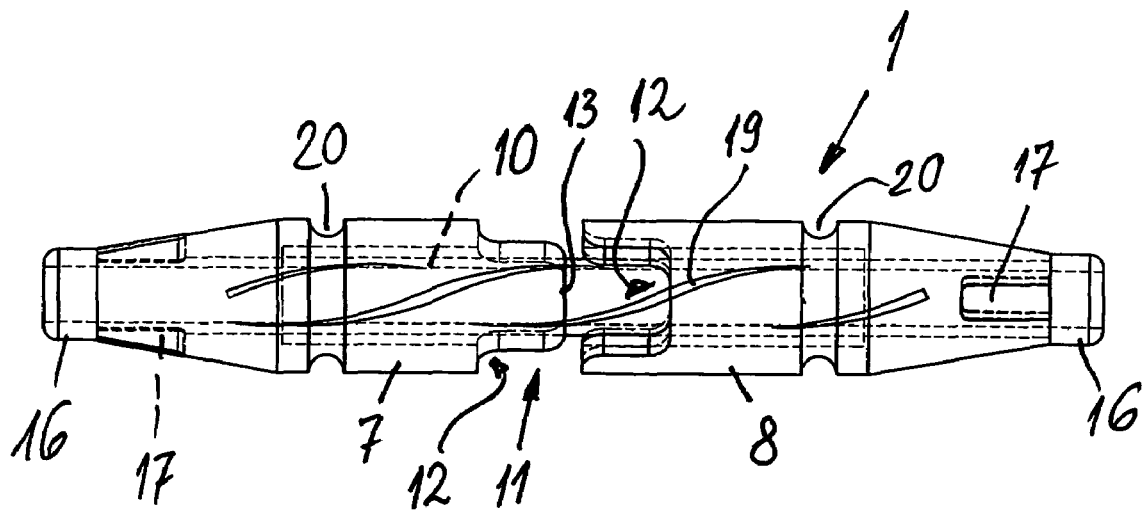
FIG. 3 is a representation according to FIG. 2, with the two parts of the sheath being pulled apart in the axial direction to such an extent that the respective tongues are moved out of the recesses so that the parts of the sheath can be rotated in reference to one another before they are guided back together axially, with the rotation distorting the elastic hose located inside and reducing it in its cross-section, so that it can grasp the electrode in a force-fitting manner.

Along a separation point 11 encircling the sheath in the circumferential direction, the sheath 9 is divided into the two parts 7 and 8 that can be moved in relation to one another in the axial direction, i.e. according to FIG. 3 the two parts 7 and 8 of the sheath can be pulled apart against the restoring force of the hose 10 so that they do no longer contact at their separation point 11.

Figure 2:
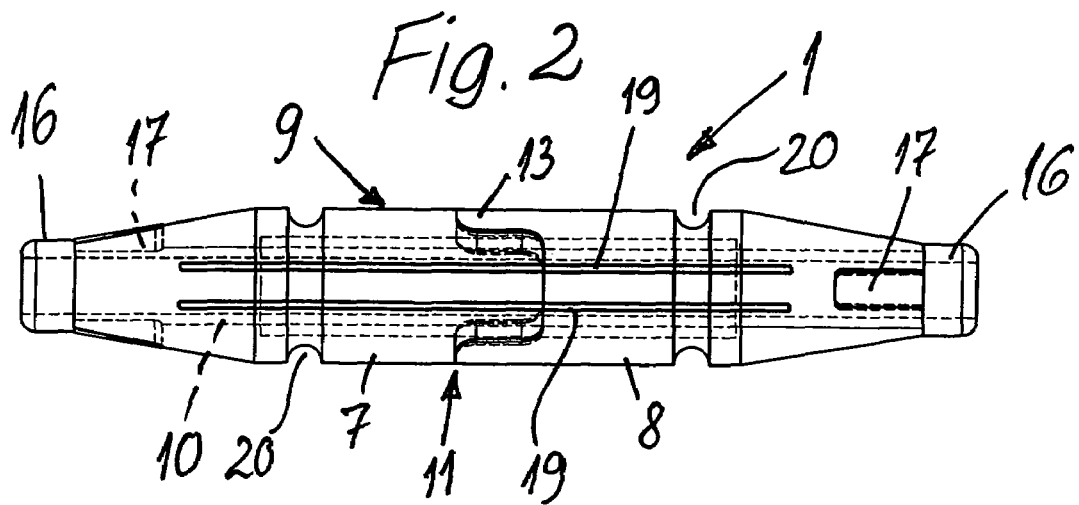
FIG. 2 is a side view of a device essentially forming a sheath, divided in the circumferential direction into two parts, with an elastically stretchable hose extending in its interior forming the interior longitudinal cavity for accepting the electrode, with the two parts of the sheath form-fittingly engaging with tongue-and recesses in the axial direction.
Figure 8:
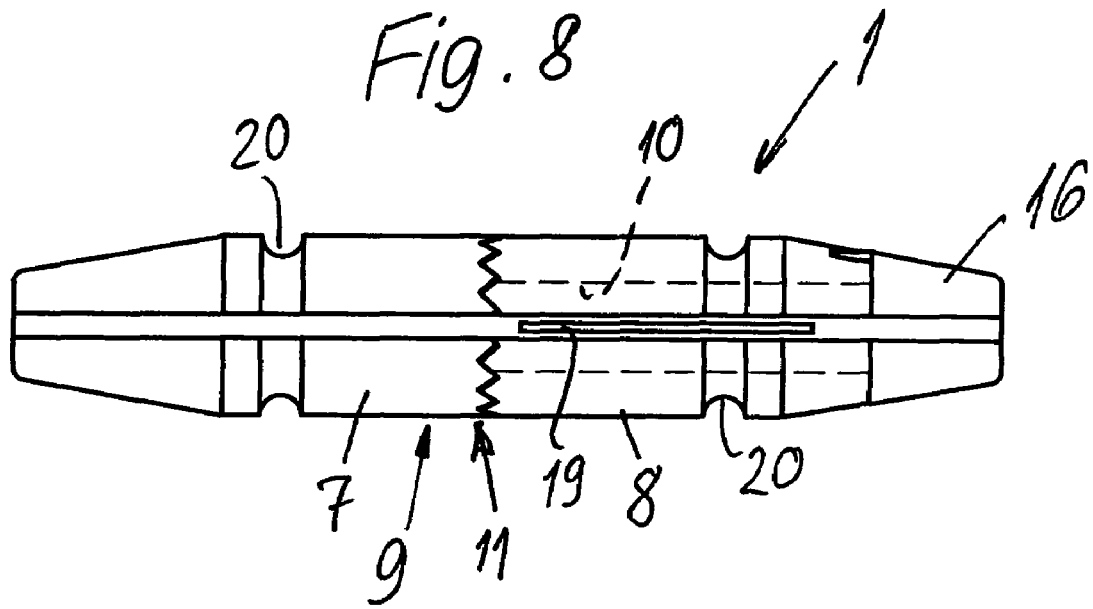
FIG. 8 is a view of a modified embodiment, in which the two parts of the sheath are toothed at their contact point to one another.
Figure 9:
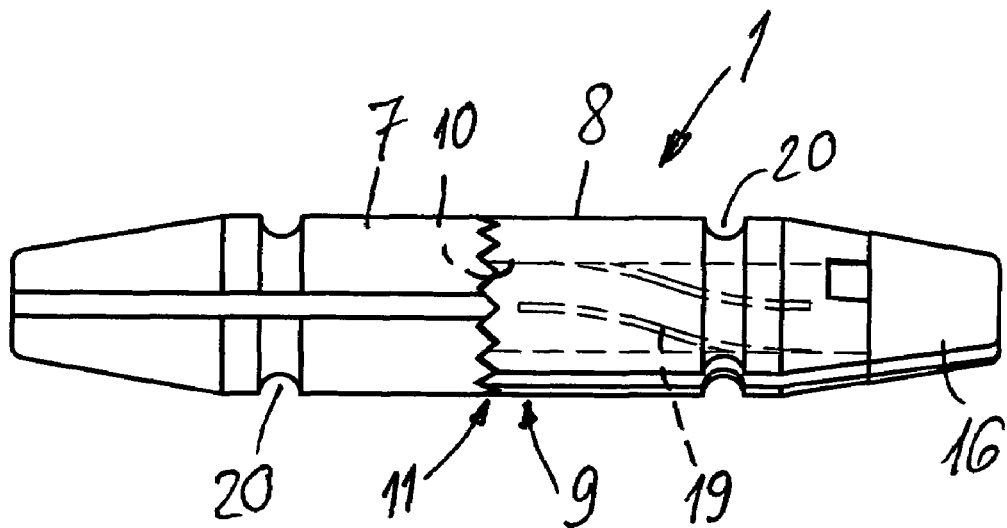
FIG. 9 is a representation according to FIG. 8 after the initial axial pulling apart, rotation, and reconnection of the two parts of the sheath, by which the hose located in the interior is distorted and reduced in its cross-section.
Figure 10:
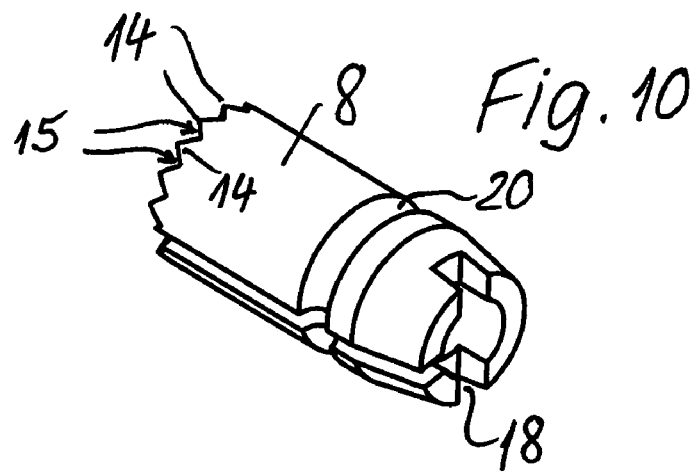
FIG. 10 is a view of a part of the sheath of the device according to FIGS. 8 and 9.

Here, in the two exemplary embodiments it is provided that the separation point 11 in reference to a diametral cross-sectional plane, has axially alternating opposing sides, so that the edges of the parts 7 and 8 of the sheath 9 contacting the faces of one another are profiled such that they are connected in the rotational direction in a form-fitting manner. The parts 7 and 8 can be separated by the already mentioned moving apart in the axial direction from their coupling mutually effective in the torsion direction, namely to the extent that the two parts now can be rotated in reference to one another distorting or twisting the elastic hose 10, and subsequently in the rotated position can be brought back into the coupling position and into a mutual contact with one another, in which they are again fastened against a rotational motion. When comparing FIGS. 2 and 3 it is discernible how the two parts 7 and 8 can be pulled apart and then be rotated, with FIG. 3 showing a position in which the mutual profiles again match together, but have not been guided together yet. Similar conditions apply for FIGS. 8 and 9 in a modified exemplary embodiment.

In the exemplary embodiment according to FIGS. 2 through 7, the profiling at the separation point 11 of the parts 7 and 8 of the sheath comprises recesses 12 and protrusions or tongues 13 extending in the axial direction, with the tongues 13 of the one part 7 form-fittingly engaging into the recesses 12 of the other part 8 and additionally the tongues 13 of part 8 into the recesses 12 of the part 7, namely by their contours such that according to FIG. 7, in spite of the separation point 11, a practically smooth and continuous or closed surface of the sheath 9 results.

Here, on the one part 7, two axially extending and in the circumferential direction slightly bent tongues 13 are arranged, and on the other part 8 two matching recesses 12 are provided, which themselves are limited by tongues 13, which can fit between the tongues 13 of the first part 7. Primarily based on FIGS. 5 through 7 it is discernible that the tongues 13 are generally provided with the same contours as the recesses 12 so that they mutually complement each other. Here, it is discernible that the tongues 13 and the recesses 12 have a regular distance from one another in the circumferential direction and that the tongue 13 and thus the recesses 12 as well are offset in reference to one another by 180°. However, more tongues and recesses may also be provided with a lesser angular distance from one another.

In the exemplary embodiment according to FIGS. 8 through 12, the parts 7 and 8 of the sheath 9 are provided with profiles of geared wheels which mutually match at the contacting edges. It is clearly discernible that these relatively many teeth 14 only require a relatively small axial motion of the two parts 7 and 8 apart from one another and that the mutual rotation can occur in small or larger steps in order to distort the hose 10 located on the inside and thus press against the electrode in a force-fitting manner.

The teeth 14 of the geared wheel portion of the parts 7 and 8 of the sheath 9 and the recesses 15 (compare FIG. 10, in particular) are embodied approximately angular or triangle-shaped in the exemplary embodiment, so that the tip of a tooth 15 fits into the respective angular tooth gap and again results in a smooth and closed surface of the sheath 9 in the operational position.

In both exemplary embodiments it is provided that end stops 16 are located on the elastic hose 10, towards the sheath 9 and/or towards the parts 7 and 8. The end stops 16 serve as an abutment for the parts 7 and 8 located between the end stops 16 on the hose 10, with a torsion lock being provided between the end stops 16 and/or the hose 10, on the one hand, and the parts 7 and 8 of the sheath 9, on the other hand, so that pulling apart the parts 7 and 8 of the sheath in the axial direction beyond the end stop 16 leads to an axial stretching of the hose 10, while subsequently the relative rotation of the parts 7 and 8 in reference to one another beyond the end stops 16 can be transferred to the hose 10, so that it twists in the desired manner and thus its interior cross-section is reduced in order to clamp or force-fittingly grasp the electrode 2.

On each of the end stops 16, a bar-shaped spring 17 is discernible protruding in the axial direction and here simultaneously protruding in the radial direction in reference to the hose 10, and which form-fittingly engage into open grooves 18 at the faces of the respective parts 7 or 8 of the sheath. It is also possible for the end stop 16 to be provided with a recess and the respective parts 7 and 8 of the sheath with a matching protrusion. Finally, the contact points of the end stops 16 and the parts 7 and 8 of the sheath can be profiled or toothed in a form-fitting matching manner. By these means, a good force transmission can be achieved primarily during the rotation of the parts of the sheath in reference to one another and thus the torsion of the hose 10 following therefrom.

In the FIGS. 2 through 4, 6, 8, 9, and 11, it is discernible in the exemplary embodiment that the elastic hose 10 is provided with several axial slits 19 extending over at least part of its length in the relaxed position, which are deformed into one or more helical lines based on the torsion of the hose caused during the rotation of the parts 7 and 8 of the sheath in reference to one another. This type of deformation is particularly well discernible in a comparison of FIGS. 2 and 3 or in the FIGS. 8 and 9 to one another, which simultaneously causes FIG. 3 showing not only their axial motion away from one another but also a rotation of the two parts 7 and 8 of the sheath in reference to one another. At the exterior of the parts 7 and 8 of the sheath a circular groove 20 is discernible each, which serves, on the one hand, for mounting suture material for fastening the device 1 in the pacemaker bed or is suitable therefore and which simultaneously facilitates the grasping and axial pulling apart of the two parts 7 and 8 of the sheath. Additionally, the exterior sides of the parts 7 and 8 of the sheath are roughened or provided with grooves or flutes or profiles in order to facilitate the opposite motion of the parts 7 and 8 of the sheath against the restoring force of the elastic hose 10.

A surgeon can also force-fittingly grasp an electrode 2 with the device 1, when it is positioned as good as possible in the heart and in the pacemaker bed and subsequently can fasten it in a conventional manner with the help of the device 1 before the entry 6 into the vein 4.

The device 1 serves to fasten an electrode 2 in the pacemaker bed before the entry 6 of the electrode 2 into a vein 4 and is provided with a sheath 9 comprising two parts 7 and 8, with a hose 10 extending in their interior. The two parts 7 and 8 of the sheath 9 are profiled at the contacting rims of a common separating point 10, so that they remain fixed in the rotational direction until a user pulls them apart beyond the axial extension of the profiling. In this pulled-apart position, the parts of the sheath can be rotated in reference to one another under a torsion of the hose and then, due to the restoring force of the hose 10, be again guided together axially, which reduces the interior cross-section of the hose and form-fittingly grasps the electrode 2 extending therethrough.

The invention claimed is:

1. A device for fastening an electrode in a pacemaker bed in a position before entry of the electrode into a vein, the device comprising a sheath, having an interior cavity extending in an axial direction therethrough for accepting the electrode, the interior cavity being reducible in cross-section for fastening the electrode in an operational position, the sheath comprising an elastic hose stretchable in the axial direction against a restoring force, which forms the interior cavity for accepting the electrode, the sheath being divided in the longitudinal direction along a circumferential separation point into at least two parts that can be moved in relation to one another in the axial direction, the circumferential separation point includes axial deviations in reference to a diametral cross-sectional plane which alternate to opposite sides such that edges of the parts of the sheath contacting at faces thereof include profiling to provide a form-fitting connection in a rotational direction and the parts can be pulled apart in the axial direction against the restoring force of the elastic hose, which contracts, to such an extent that the engaged profiling is disengaged and the two parts can be rotated against torsion or twisting of the elastic hose and are refastened against rotational movement by re-engaging in a rotated position.

2. A device according to claim 1, wherein the profiling at the separation point of the parts of the sheath is comprised of recesses and protrusions or tongues, which extend in the axial direction, with the protrusions or tongues of the one part fitting, in a form-fitting manner, into the recesses of the other part.

3. A device according to claim 2, wherein there are two of the tongues or protrusions on the one part which extend in the axial direction and that on the other part there are two of the matching recesses, limited by tongues or protrusions of the other part which fit between the tongues or protrusions of the first part.

4. A device according to claim 2, wherein the tongues or protrusions and the recesses are spaced apart at a regular distance from one another in the circumferential direction, and the tongues or protrusions are arranged offset equally from one another.

5. A device according to claim 1, wherein the parts of the sheath are provided at the contacting edges with mutually matching gear wheels.

6. A device according to claim 5, wherein teeth of the gear wheels on the parts of the sheath and gaps between the teeth are formed with an angular or triangle-shape, and tips of the teeth fit into respective ones of the angular gaps.

7. A device according to claim 1, wherein end stops are provided on the elastic hose which serve as abutment for the parts of the sheath arranged between the end stops, with a rotation lock being provided between at least one of the end stops or the hose and the parts of the sheath.

8. A device according to claim 7, wherein a bar-shaped spring protrudes at the end stops in the axial direction, and form-fittingly fits into an open groove of the corresponding part of the sheath.

9. A device according to claim 1, wherein the elastic hose is provided with one or more slits extending axially in a relaxed state of the elastic hose, over at least a part of a length thereof, the slits are deformed during rotation of the parts of the sheath into one or more approximately helical lines.

10. A device according to claim 1, wherein an exterior of the parts of the sheath are at least one of roughened, provided with grooves, flutes or profiling.

11. A device according to claim 10, wherein the exterior of at least one of the parts of the sheath is provided with a circular groove for mounting suture material adapted for fastening the device in the pacemaker bed.

12. A device according to claim 7, wherein the end stop is provided with a recess, and protrusions located on the parts engage in an operational position with the end stops.

13. A device according to claim 7, wherein the parts of the sheath are profiled and engage in a form-fitting manner with the end stops.

* * * * *